(12) United States Patent
De La Poterie et al.

(10) Patent No.: US 7,867,504 B2
(45) Date of Patent: *Jan. 11, 2011

(54) FILM-FORMING COSMETIC COMPOSITION

(75) Inventors: Valérie De La Poterie, Le Chatelet en Brie (FR); Jean Mondet, Aulnay Sous Bois (FR); Frédéric Auguste, Chevilly-Larue (FR)

(73) Assignee: L'Oreal S.A., Paris (FR)

( * ) Notice: Subject to any disclaimer, the term of this patent is extended or adjusted under 35 U.S.C. 154(b) by 1106 days.

This patent is subject to a terminal disclaimer.

(21) Appl. No.: 09/881,097

(22) Filed: Jun. 15, 2001

(65) Prior Publication Data

US 2002/0041857 A1   Apr. 11, 2002

(30) Foreign Application Priority Data

Jun. 15, 2000  (FR) .................................. 00 07658

(51) Int. Cl.
*A61K 8/02* (2006.01)
*A61K 8/00* (2006.01)

(52) U.S. Cl. ..................... 424/401; 424/70.1
(58) Field of Classification Search ................ 424/401, 424/59, 61, 63, 64, 70.7, 78.03
See application file for complete search history.

(56) References Cited

U.S. PATENT DOCUMENTS

| | | | |
|---|---|---|---|
| 3,937,811 A | 2/1976 | Papantoniou et al. | |
| 4,423,031 A | 12/1983 | Murui et al. | |
| 5,273,757 A | 12/1993 | Jaeger et al. | |
| 5,312,865 A * | 5/1994 | Hoefer et al. | 524/591 |
| 5,411,739 A | 5/1995 | Jaeger et al. | |
| 5,711,940 A | 1/1998 | Kuentz et al. | |
| 5,817,304 A | 10/1998 | Mondet et al. | |
| 5,851,517 A * | 12/1998 | Mougin et al. | 424/401 |
| 6,264,933 B1 * | 7/2001 | Bodelin et al. | 424/401 |
| 6,333,053 B1 * | 12/2001 | Simon | 424/401 |
| 6,335,003 B1 * | 1/2002 | Kim et al. | 424/70.17 |
| 6,432,527 B1 * | 8/2002 | Perez et al. | 428/343 |

FOREIGN PATENT DOCUMENTS

| | | |
|---|---|---|
| EP | 0 305 756 | 3/1989 |
| EP | 0 367 015 | 5/1990 |
| EP | 0 749 747 | 12/1996 |
| EP | 0 873 748 | 10/1998 |
| EP | 0 943 310 | 9/1999 |
| EP | 0 979 642 | 2/2000 |
| EP | 0 993 824 | 4/2000 |
| FR | 2 232 303 | 1/1975 |
| FR | 2 710 646 | 4/1995 |
| FR | 2 771 927 | 6/1999 |
| FR | 2 782 917 | 3/2000 |
| WO | WO 95/15741 | 6/1995 |
| WO | WO 96/33690 | 10/1996 |
| WO | WO 99/39688 | 8/1999 |

OTHER PUBLICATIONS

Eric A. Grulke, "Solubility Parameter Values", Polymer Handbook, Third Edition, John Wiley & Sons, 1989, pp. 519-559.
Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104-117.
Co-pending Application—Title: Film-Forming Cosmetic Composition Inventor(s): Valérie De La Poterie et al. U.S. Filing Date: Jun. 15, 2001.
English language Derwent Abstract of EP 0 873 748, Oct. 28, 1998.
English language Derwent Abstract of EP 0 943 310, Sep. 22, 1999.
English language Derwent Abstract of EP 0 979 642, Feb. 16, 2000.
English language Derwent Abstract of EP 0 993 824, Apr. 19, 2000.
English language Derwent Abstract of FR 2 771 927, Jun. 11, 1999.
English language Derwent Abstract of FR 2 782 917, Mar. 10, 2000.

* cited by examiner

*Primary Examiner*—Sreeni Padmanabhan
*Assistant Examiner*—Layla Soroush
(74) *Attorney, Agent, or Firm*—Finnegan, Henderson, Farabow, Garrett & Dunner, L.L.P.

(57) ABSTRACT

A composition comprising, in a physiologically acceptable medium, at least one film-forming polymer and at least one thermal transition agent which undergoes a change of state at a transition temperature Tt chosen within a temperature range from 25° C. to 80° C., the at least one thermal transition agent being insoluble in water maintained at a temperature below the transition temperature, Tt, the at least one film-forming polymer and the at least one thermal transition agent are present in an amount which is sufficient so that the composition is capable of forming a film at the temperature of a keratinous material to which the composition is applied, wherein the film has a resistance (Rc) to hot water (40° C.) of less than or equal to 15 minutes and a resistance (Rf) to cold water (20° C.) such that Rf–Rc≧8 minutes. The invention also relates to a cosmetic care or make-up process for a keratinous material. The composition makes it possible to obtain a film which is resistant to cold water and which can be removed simply with hot water.

56 Claims, No Drawings

FILM-FORMING COSMETIC COMPOSITION

The present invention relates to a cosmetic composition forming a film which may exhibit at least one of good resistance to cold water and removability with hot water, comprising at least one film-forming polymer and at least one thermal transition agent. The invention also relates to a make-up or cosmetic care composition for keratinous materials, for example, human keratinous materials chosen from skin, eyelashes, eyebrows, hair and nails.

The composition may be in the form chosen, for example, from a mascara, an eyeliner, a product for the lips, a blusher, an eyeshadow, a foundation, a make-up product for the body, a concealer product, a product for the nails, an anti-sun composition, a skin coloring composition and a skincare product. In one embodiment of the invention, the composition is a mascara.

Mascara compositions in the form of a wax-in-water emulsion comprising surfactants are known from document WO-A-95/15741. However, the make-up film obtained with these compositions may not show good water resistance and when the film comes into contact with water, for example when bathing or taking a shower, it may partially disintegrate by being worn away or by spreading around the eyes. The wearing away of the film may give rise to a substantial reduction in the intensity of the color of the make-up, thus obliging the consumer to freshen the application of the mascara. Spreading of the film may form a very unsightly aureole around the area to which make-up has been applied. Tears and perspiration may also cause these same drawbacks.

To promote the water resistance of make-up, it is known practice from U.S. Pat. No. 4,423,031 to use acrylic polymers in aqueous dispersion. However, the mascara may be difficult to remove and may require special make-up removers comprising oils or organic solvents. These make-up removers may be irritating to eyes, for example, they may cause stinging, they may leave a veil over the eyes, or they may leave an uncomfortable greasy residual film on the skin around the eyes (eyelids).

To avoid the use of these special make-up removers, it is possible to use soap and water, as disclosed in document WO-A-96/33690, with a mascara comprising a water-insoluble polymer and a water-soluble film-forming polymer. However, the use of soap may cause eye discomfort by stinging or by depositing a veil over the eyes. Soap may also dissolve the make-up film, which can then spread around the eyes to form unsightly aureoles and skin staining.

The use of hot water, that is to say, water with a temperature of at least 35° C. (temperature measured at atmospheric pressure), ranging, for example, from 35° C. to 50° C., makes it possible to avoid the drawbacks of the make-up removers known hitherto. However, the cold-water-resistant mascara compositions described previously can be difficult to remove with hot water.

The present invention relates to a cosmetic composition which may have at least one of the following properties: may be removed with hot water and may have good cold-water resistance.

The inventors have discovered that such a composition may be obtained using at least one film-forming polymer and at least one thermal transition agent. After applying the composition to keratinous materials, for example, eyelashes, the make-up obtained exhibits at least one of the following properties: good resistance to cold water (water with a temperature less than or equal to 30° C., for example, when bathing), resistance to tears, and resistance to perspiration. The make-up can be easily removed with hot water, for example, by rubbing with cotton wool or gauze. The make-up can be detached easily from the eyelashes and removed from the eyelashes without fragmenting into forms such as a sheath, fragments and pieces. The make-up thus removed does not spread on the skin, avoiding the formation of aureoles around the eye. When removing the make-up, the skin remains clean. The make-up may be removed simply with hot water and for example, with hot water containing no detergent such as soaps. For the make-up removal, the hot water used may be chosen, for example, from tap water, demineralized water and mineral water brought to a temperature of at least 35° C., such as, for example ranging from 35° C. to 50° C.

One embodiment of the invention is a composition comprising, in a physiologically acceptable medium, at least one film-forming polymer and at least one thermal transition agent which undergoes a change of state at a transition temperature, Tt, chosen within a temperature range, for example, from 25° C. to 80° C., the at least one thermal transition agent being not water soluble, as defined below,=in water maintained at a temperature below the transition temperature, Tt, wherein the at least one film-forming polymer and the at least one thermal transition agent are present in the composition according to the invention an amount, for example, sufficient so that the composition is capable, at the temperature of the keratinous materials, of forming a film having a resistance (Rc) to hot water, maintained at 40° C., of less than or equal to 15 minutes and a resistance (Rf) to cold water, maintained at 20° C., such that Rf−Rc≧8 minutes, and further wherein said at least one film-forming polymer and said at least one thermal transition agent are the same or different.

One embodiment of the invention is a cosmetic care or make-up process for keratinous materials, comprising the application of a composition as defined above to the keratinous materials.

Another embodiment of the invention is the use of a composition as defined above to obtain a film deposited on the keratinous materials, wherein the composition may be at least one of resistant to cold water and removable with hot water.

Yet another embodiment of the invention is a cosmetic process for removing make-up from made-up keratinous materials with a composition as defined above, comprising at least one step of rinsing the made-up keratinous materials with hot water maintained at a temperature of at least 35° C.

The expression "physiologically acceptable" may be understood to include a medium which is compatible with keratinous materials, for example, a cosmetic medium.

The composition according to the invention is capable, at the temperature of keratinous materials, of forming a film having a resistance (Rc) to hot water maintained at 40° C. of less than or equal to 15 minutes, for example, less than or equal to 12 minutes and further still, less than or equal to 10 minutes. Thus, the film is easily removed with hot water, without using a detergent such as soaps.

The film obtained with the composition according to the invention may also have a resistance (Rf) to cold water maintained at 20° C. such that=Rf−Rc≧8 minutes such as, for example Rf−Rc≧10 minutes. In one embodiment, the film may have a resistance to cold water ranging, for example, from 8 to 120 minutes, such as, from 23 to 120 minutes. Such a film has good resistance to cold water.

The water resistance of the film may be measured according to the test protocol defined below before the examples.

In another embodiment, the composition according to the invention may contain little or no emulsifier (surfactant), for example, the emulsifier is present in the composition in an amount less than 0.5% by weight relative to the total weight of the composition. Such a composition has good resistance to cold water.

The term "emulsifier" may indicate any amphiphilic compound chosen from nonionic amphiphilic compounds with an HLB (hydrophilic-lipophilic balance) greater than or equal to 10 and ionic amphiphilic compounds with a hydrophilic portion comprising a counterion with a molar mass greater than or equal to 50 g/mol.

The make-up removal with hot water can be obtained using at least one thermal transition agent which undergoes a change of state at a temperature, Tt, chosen within a temperature ranging, for example, from 25° C. to 80° C., such as from 25° C. to 60° C. and further still from 30° C. to 60° C.

The at least one thermal transition agent above its thermal transition temperature, Tt, and after its change of state occurs, may make the film more water-sensitive. That is, the film of make-up becomes brittle on contact with hot water and by rubbing it, for example with fingers, a cloth or cotton wool, the film readily disintegrates or detaches from its support.

The term "water-soluble" as applied to a thermal transition agent indicates a thermal transition agent with a solubility of more than 1% by weight in one liter of water at a temperature below the transition temperature of the thermal transition agent. The term "not water-soluble" as applied to a thermal transition agent indicates a thermal transition agent with a solubility less than or equal to 1% by weight when dissolved in one liter of water at a temperature below the transition temperature of the thermal transition agent.

The change of state may be, for example, a change in the arrangement of the atoms, a change of atomic ionisation, or a change in the cohesion of the atoms, such as a change from solid to liquid or liquid to gas. According to an embodiment according to the invention, the change of state may be the passage from a solid state to a liquid state (by melting). The at least one thermal transition agent may be a compound chosen, for example, from crystalline and semi-crystalline compounds with a melting point ranging from 25° C. to 80° C., such as from 25° C. to 60° C., and further still, ranging from 30° C. to 60° C. This melting point may be measured using a differential scanning calorimeter (D.S.C.).

Non-limiting examples of crystalline compounds which may be used are polyethylene waxes, for example, a polyethylene wax with a weight-average molecular weight of less than or equal to 400, such as the product sold under the name "PERFORMALENE 400" by the company Petrolite.

According to another embodiment of the invention, the change of state may be the passage from an associated state to a dissociated state due to the provision of hot water. For example, the change of state may be brought about by hydration, giving rise to the dissociation of the at least one thermal transition agent.

The at least one thermal transition agent may be a compound, for example, a polymer, with a hydroxyl number of at least 5, such as, ranging from 5 to 300 and further still, a hydroxyl number of at least 25 (such as ranging from 25 to 200). Such at least one thermal transition agent may be readily dispersed in water without using an emulsifier.

The polymer with a hydroxyl number of at least 5, for example, may have a weight-average molecular weight of less than or equal to 10,000, such as, for example, in a range of 500 to 5000.

The expression "hydroxyl number of a compound" may be understood to indicate the amount of potassium hydroxide (KOH) expressed in mg required to neutralize the acetic acid released after hydrolysis of 1 gram of acetylated compound.

For example, the at least one thermal transition agent may be polycaprolactones chosen from ε-caprolactone homopolymers. The homopolymerization may be initiated with a diol, for example, a diol containing from 2 to 10 atoms, chosen, for example, from diethylene glycol, 1,4-butanediol and neopentyl glycol.

The polycaprolactones sold under the name CAPA® 240, 223, 222, 217, 215, 212, 210 and 205 by the company Solvay, and PCL-300 and PCL-700 by the company Union Carbide may be used, for example.

The at least one thermal transition agent may be present in the composition according to the invention, in an amount ranging for example, from 0.1% to 30% by weight relative to the total weight of the composition, such as, from 0.5% to 25% by weight and further still from 1% to 20% by weight, or even further still from 3% to 15% by weight relative to the total weight of the composition.

According to one embodiment variant of the composition according to the invention, the at least one film-forming polymer and the at least one thermal transition agent may be one and the same compound.

According to the invention, the composition comprises at least one film-forming polymer, also known as the at least one first film-forming polymer.

In the present application, the term "film-forming polymer" may be understood to indicate a polymer which is capable, by itself or in the presence of an auxiliary film-forming agent, of forming a continuous film which adheres to a support, for example, to keratinous materials.

The at least one film-forming polymer present in the composition according to the invention may be chosen from hydrophobic and water-soluble film-forming polymers.

The term "hydrophobic film-forming polymer" may be understood to indicate a polymer with a solubility of less than 1% by weight when dissolved in one liter of water at 25° C. The term "water-soluble film forming polymer" may be understood to indicate a polymer with a solubility of at least 1% by weight when dissolved in one liter of water at 25° C.

A hydrophobic film-forming polymer may be used, for example, as the at least one film-forming polymer so that a film with good resistance to cold water is obtained.

The at least one first film-forming polymer may be at least one chosen, for example, from synthetic polymers, such as, free-radical polymers and polycondensates, and polymers of natural origin.

The term "free-radical film-forming polymer" may be understood to indicate a polymer obtained by polymerization of monomers containing unsaturation, for example, ethylenic unsaturation (unlike polycondensates).

The at least one film-forming polymers of free-radical type may be chosen, for example from vinyl polymers and vinyl copolymers, such as, acrylic polymers.

The vinyl polymers may result from the polymerization of at least one monomer chosen from monomers with ethylenic unsaturation containing at least one acidic group (acid monomers), esters of these acid monomers and amides of these acid monomers.

As monomers with ethylenic unsaturation containing at least one acidic group, it is possible to use α,β-ethylenic unsaturated carboxylic acids chosen, for example, from acrylic acid, methacrylic acid, crotonic acid, maleic acid and itaconic acid. In one embodiment, (meth)acrylic acid and crotonic acid are used, and in another embodiment, (meth)acrylic acid is used.

The esters of acid monomers may be chosen from (meth)acrylic acid esters (also referred to as (meth)acrylates), for example, alkyl (meth)acrylates, wherein the alkyl group is chosen from linear, branched and cyclic ($C_1$-$C_{30}$) alkyls, such as, for example, ($C_1$-$C_{20}$) aryl (meth)acrylates, and further still ($C_6$-$C_{10}$) aryl (meth)acrylates), and hydroxyalkyl (meth)acrylates, for example, ($C_2$-$C_6$) hydroxyalkyl (meth)acrylates.

Among the alkyl (meth)acrylates which may be mentioned are those chosen from methyl methacrylate, ethyl methacrylate, butyl methacrylate, isobutyl methacrylate, 2-ethylhexyl methacrylate and lauryl methacrylate.

Among the hydroxyalkyl (meth)acrylates which may be mentioned are those chosen from hydroxyethyl acrylate, 2-hydroxypropyl acrylate, hydroxyethyl methacrylate and 2-hydroxypropyl methacrylate.

Among the aryl (meth)acrylates which may be mentioned are those chosen from benzyl acrylate and phenyl acrylate.

The (meth)acrylic acid esters are chosen, for example, from alkyl (meth)acrylates.

According to the present invention, the alkyl group of the esters may be chosen, for example, from fluorinated and perfluorinated alkyl groups, that is to say that some or all of the hydrogen atoms of the alkyl group are replaced with fluorine atoms.

Non-limiting examples of amides of the acid monomers which may be mentioned are those chosen from (meth)acrylamides, for example, N-alkyl(meth)acrylamides, such as ($C_1$-$C_{20}$)alkyls. Among the N-alkyl(meth)acrylamides which may be mentioned are those chosen from N-ethylacrylamide, N-t-butylacrylamide, N-t-octylacrylamide and N-undecylacrylamide.

The vinyl polymers of the at least one film-forming polymer may also result from the homopolymerization or copolymerization of at least one monomer chosen from vinyl esters, olefins (including fluoroolefins), vinyl ethers, and styrene monomers. For example, these monomers may be copolymerized with at least one of acid monomers, esters thereof, and amides thereof, such as those mentioned above.

Non-limiting examples of vinyl esters which may be mentioned are chosen from vinyl acetate, vinyl neodecanoate, vinyl pivalate, vinyl benzoate and vinyl t-butyl-benzoate.

Among the olefins which may be mentioned are those chosen, for example, from ethylene, propylene, butene, isobutene, octene, octadecene, and polyfluorinated olefins chosen, for example, from tetrafluoroethylene, vinylidene fluoride, hexafluoropropene and chlorotrifluoroethylene.

Styrene monomers which may be mentioned are chosen, for example, from styrene and α-methylstyrene.

The list of monomers given is not limiting, and it is possible to use any monomer known to those skilled in the art which falls within the categories of acrylic and vinyl monomers (including monomers modified with a silicone chain).

Non-limiting representatives of at least one film-forming polymer, include at least one polycondensate chosen from anionic, cationic, non-ionic, and amphoteric polyurethanes, polyurethane-acrylics, polyurethane-polyvinyl pyrrolidones, polyester-polyurethanes, polyether-polyurethanes, polyureas and polyurea/polyurethanes.

The polyurethanes may be for example, at least one chosen from aliphatic, cycloaliphatic, and aromatic polyurethanes, polyurea/urethanes, and polyurea copolymers comprising at least one of:
  at least one sequence of at least one aliphatic polyester origin, cycloaliphatic polyester origin, and aromatic polyester origin
  at least one branched and unbranched silicone sequence, for example, from polydimethylsiloxane and polymethylphenylsiloxane, and
  at least one sequence comprising fluorinated groups.

Additional non-limiting representatives of polycondensates may be chosen from polyesters, polyesteramides, fatty-chain polyesters, polyamides resins, epoxyester resins, arylsulphonamide-epoxy resins, and resins resulting from the condensation of formaldehyde with an arylsulphonamide.

The polyesters may be obtained, in a known manner, by polycondensation of dicarboxylic acids with polyols, for example diols.

The dicarboxylic acids may be chosen, for example, from aliphatic, alicyclic and aromatic dicarboxylic acids. Non-limiting examples of dicarboxylic acids which may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, diglycolic acid, thiodipropionic acid, 2,5-naphthalenedicarboxylic acid, and 2,6-naphthalenedicarboxylic acid. These dicarboxylic acid monomers may be used alone or as a combination of at least two dicarboxylic acid monomers. Among these monomers, the ones, for example, from phthalic acid, isophthalic acid and terephthalic acid.

The diols may be chosen from aliphatic, alicyclic, and aromatic diols. The diols used may be chosen, for example, from ethylene glycol, diethylene glycol, triethylene glycol, 1,3-propanediol, cyclohexanedimethanol and 4-butanediol. Other non-limiting examples of polyols which may be used may be chosen from glycerol, pentaerythritol, sorbitol and trimethylolpropane.

The polyesteramides may be obtained in a manner similar to that of the polyesters, by polycondensation of diacids with diamines and amino alcohols. Non-limiting examples of diamines which may be used are chosen from ethylenediamine, hexamethylenediamine, meta-phenylenediamine and para-phenylenediamine. An amino alcohol which may be used is monoethanolamine.

The polyesters may also comprise at least one monomer bearing at least one group —$SO_3M$, wherein M is chosen from a hydrogen atom, an ammonium ion $NH_4^+$, and a metal ion chosen from, for example, $Na^+$, $Li^+$, $K^+$, $Mg^{2+}$, $Ca^{2+}$, $Cu^{2+}$, $Fe^{2+}$ and $Fe^{3+}$ ions. A difunctional aromatic monomer comprising a group —$SO_3M$ may be used, for example.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. Examples of difunctional aromatic monomers also bearing a group —$SO_3M$ which may be mentioned include: sulphoisophthalic acid, sulphoterephthalic acid, sulphophthalic acid, and 4-sulphonaphthalene-2,7-dicarboxylic acid.

In the compositions which are the subject of the invention, it is possible to use copolymers based on isophthalate/sulphoisophthalate, such as, for example, copolymers obtained by condensation of di-ethylene glycol, cyclohexanedimethanol, isophthalic acid and sulphoisophthalic acid. Such polymers are sold, for example, under the brand name EASTMAN AQ by the company Eastman Chemical Products.

The at least one hydrophobic film-forming polymer of synthetic origin may also be a silicone polymer, for example polyorganopolysiloxane.

The film-forming polymer of natural origin, which can be optionally modified, may be chosen from at least one of: shellac resin, sandarac gum, dammar resins, elemi gums, copal resins, and polymers of cellulose derivatives chosen from nitrocellulose, cellulose acetate, cellulose acetobutyrate, cellulose acetopropionate and ethylcellulose.

According to one embodiment variant of the invention, the at least one first polymer may be present in the form of particles dispersed in an aqueous medium. The expression "polymer in the form of particles in aqueous dispersion", which is generally known as a latex or pseudolatex, may be understood to include a phase containing water and optionally a water-soluble compound, in which is directly dispersed the polymer in the form of particles. The term "water-soluble compound" indicates a compound with a solubility of at least 1% by weight when dissolved in one liter of water at 25° C.

The size of the polymer particles in aqueous dispersion may range, for example, from 10 nm to 500 nm, such as, from 20 nm to 300 nm.

The aqueous medium may comprise water and may also comprise a mixture of water and of water-miscible solvent, chosen, for example, from lower monoalcohols containing from 1 to 5 carbon atoms, glycols containing from 2 to 8 carbon atoms, ($C_3$-$C_4$) ketones and ($C_2$-$C_4$)aldehydes. The aqueous medium may be present in the composition in an amount ranging, for example, from 5% to 94.9% by weight relative to the total weight of the composition.

Non-limiting representatives of film-forming polymers in aqueous dispersion which may be used include the acrylic polymers sold under the names NEOCRYL XK-90®, NEOCRYL A-1070®, NEOCRYL A-1090®, NEOCRYL BT-62®, NEOCRYL A-1079® and NEOCRYL A-523® by the company Zeneca, DOW LATEX 432® by the company Dow Chemical, polyurethanes chosen, for example, from polyester-polyurethanes sold under the names "AVALURE UR-405®", "AVALUREUR-410®", "AVALURE UR-425®" and "SANCURE 2060®" by the company Goodrich, polyether-polyurethanes sold under the names "SANCURE 878®" and "AVALURE UR-450®" by the company Goodrich and "NEOREZ R-970®" by the company ICI and polyurethane-acrylics sold under the name NEOREZ R-989® by the company Zeneca.

It is also possible to use "alkali-soluble" polymers, taking care to ensure that the pH of the composition is adjusted so as to keep these polymers in the form of particles in aqueous dispersion. The term "alkali-soluble polymer" indicates a polymer with a solubility of at least 1% by weight when dissolved in one liter of alkaline solution at 25° C.

The composition according to the invention may comprise at least one film-forming auxiliary agent which promotes the formation of a film with the particles of the at least one film-forming polymer. The at least one film-forming agent may be chosen from any compounds known to those skilled in the art as being capable of fulfilling the desired function, and may be chosen, for example, from plasticizers and coalescers.

According to another embodiment variant of the invention, the at least one first film-forming polymer may be present in the form of surface-stabilized particles dispersed in a liquid fatty phase. The size of the particles of the at least one first film-forming polymer dispersed in the liquid fatty phase may range, for example, from 10 nm to 500 nm, such as, from 20 nm to 300 nm.

For example, the liquid fatty phase can comprise a volatile liquid fatty phase, optionally mixed with a non-volatile liquid fatty phase.

The expression "volatile fatty phase" may be understood to include any non-aqueous medium which is capable of evaporating from the skin in less than one hour. The volatile phase, for example, may comprise oils with a vapor pressure, at room temperature and atmospheric pressure, ranging from $10^{-3}$ to 300 mm Hg (0.13 Pa to 40,000 Pa).

The liquid fatty phase in which the polymer is dispersed may comprise any physiologically acceptable oil and for example, cosmetically acceptable oils chosen from oils of mineral origin, animal origin, plant origin, and synthetic origin, carbon-based oils, hydrocarbon-based oils, fluoro oils and silicone oils, alone or as a mixture provided that they form a homogeneous and stable mixture and provided that they are compatible with the intended use.

The total liquid fatty phase may be present in the composition according to the invention, in an amount ranging, for example, from 5% to 98% by weight relative to the total weight of the composition, such as, from 20% to 85% by weight. The non-volatile part of the liquid fatty phase may be present in the composition according to the invention in an amount ranging, for example, from 0 to 80%, such as from 0.1% to 80%, by weight relative to the total weight of the composition and further still, from 1% to 50% by weight relative to the total weight of the composition.

Non-limiting representatives of liquid fatty phases which may be used in the invention are chosen, for example, from fatty acid esters; higher fatty acids; higher fatty alcohols; polydimethylsiloxanes (PDMSs), which are optionally phenylated chosen, for example, from phenyltrimethicones, which are optionally substituted with aliphatic and aromatic groups, which may be fluorinated; which are optionally substituted with functional groups chosen, for example, from at least one of hydroxyl, thiol and amine groups; polysiloxanes modified with at least one of fatty acids, fatty alcohols, and polyoxyalkylenes; fluorosilicones; and perfluoro oils.

At least one oil that is volatile at room temperature may be used. After evaporating off the oil, a non-sticky, supple film-forming deposit may be obtained. The volatile oil may also make it easier to apply the composition to keratinous fibers, for example, eyelashes.

The volatile oil may be chosen, for example, from hydrocarbon-based oils and silicone oils optionally comprising alkyl and alkoxy groups at the end of the silicone chain or pendent on the chain.

As volatile silicone oils which can be used in the invention, mention may be made of linear and cyclic silicones containing from 2 to 7 silicon atoms, these silicones optionally comprising alkyl groups and alkoxy groups containing from 1 to 10 carbon atoms. Mention may be made, for example, of octamethylcyclotetrasiloxane, decamethylcyclopentasiloxane, hexadecamethylcyclohexasiloxane, heptamethylhexyltrisiloxane and heptamethyloctyltrisiloxane.

Volatile hydrocarbon-based oils which may be mentioned are ($C_8$-$C_{16}$) isoparaffins, such as, ISOPARS and PERMETYLS, for example, isododecane.

These volatile oils may be present in the composition according to the invention in an amount ranging, for example, from 5 to 94.9% by weight relative to the total weight of the composition, such as from 20 to 85% by weight relative to the total weight of the composition.

In one embodiment of the invention, the liquid fatty phase may be at least one group chosen from:

non-aqueous liquid compounds having a global solubility parameter according to the Hansen solubility space of less than 17 $(MPa)^{1/2}$, and monoalcohols having a global solubility parameter according to the Hansen solubility space of less than or equal to 20 $(MPa)^{1/2}$.

The global solubility parameter, δ global, according to the Hansen solubility space is defined in the article "Solubility Parameter Values" by Eric A. Grulke in the book "Polymer Handbook" 3rd Edition, Chapter VII, pages 519-559 (incorporated by reference herein), by the relationship:

$$\delta = (d_D^2 + d_P^2 + d_H^2)^{1/2}$$

wherein:
- $d_D$ is the London dispersion forces arising from the formation of dipoles induced during molecular impacts,
- $d_P$ is the Debye interaction forces between permanent dipoles, and
- $d_H$ is the force of specific interactions (chosen, for example, from hydrogen bonding, acid/base bonding, donor/acceptor bonding, etc.).

The definition of solvents in the three-dimensional solubility space according to Hansen is described in the article by C. M. Hansen: "The Three-Dimensional Solubility Parameters", J. Paint Technol. 39, 105 (1967), incorporated by reference, herein.

Oils which may be used in the liquid fatty phase are mentioned, for example, in patent application EP-A-749 747, incorporated by reference, herein. Non-aqueous media which can also be used are those disclosed in document FR-A-2 710 646 from L.V.M.H., incorporated by reference, herein.

The choice of the non-aqueous medium is made by a person skilled in the art on the basis of the nature of the monomers constituting the polymer and the nature of the at least one stabilizer.

The polymer dispersion may be manufactured as disclosed in document EP-A-749 747, incorporated by reference, herein. The polymerization may be carried out in dispersion, that is to say, by precipitating the polymer as it is formed, with protection of the particles formed with at least one stabilizer as indicated below.

The polymer particles are surface-stabilized by means of at least one stabilizer which may be chosen, for example, from block polymers, grafted polymers and random polymers.

Among the grafted polymers which may be mentioned, for example, are silicone polymers grafted with a hydrocarbon-based chain, and hydrocarbon-based polymers grafted with a silicone chain.

Copolymers that are also suitable are grafted copolymers having, for example, an insoluble skeleton of polyacrylic type with soluble grafts of poly(12-hydroxystearic acid) type.

Other non-limiting representatives of copolymers which may be used include grafted block copolymers or block copolymers comprising at least one block of polyorganosiloxane type and at least one block of a free-radical polymer, for instance, grafted copolymers of acrylic/silicone type which may be used, for example, when the non-aqueous medium is a silicone medium.

The at least one stabilizer may also be chosen, for example, from grafted block copolymers and block copolymers comprising at least one block of polyorganosiloxane type and at least one block of a polyether type. The polyorganopolysiloxane block may be, for example, chosen from polydimethylsiloxanes and poly($C_2$-$C_{18}$)alkylmethylsiloxanes. The polyether block may be chosen from poly($C_2$-$C_{18}$)alkylenes, such as, for example, polyoxyethylene and polyoxypropylene. For example, dimethicone copolyols and ($C_2$-$C_{18}$) alkylmethicone copolyols may be used. It is possible, for example, to use the dimethicone copolyol sold under the name "DOW CORNING 3225C" by the company Dow Corning and the laurylmethicone copolyol sold under the name "DOW CORNING Q2-5200" by the company Dow Corning.

Grafted block copolymers and block copolymers which may be used include copolymers comprising at least one block resulting from the polymerization of at least one ethylenic monomer optionally containing at least one conjugated ethylenic bond chosen, for example, from ethylene, butadiene and isoprene, and of at least one block of a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these block copolymers which may be mentioned are, for example, copolymers of "diblock" and "triblock" type chosen from polystyrene/polyisoprene and polystyrene/polybutadiene types, such as, for example, copolymers sold under the name "LUVITOL HSB" by BASF, polystyrene/copoly(ethylene-propylene) type such as, for example, copolymers sold under the name "KRATON" by Shell Chemical Co., and polystyrene/copoly(ethylene-butylene) type.

Non-limiting representatives of grafted block copolymers and block copolymers comprising at least one block resulting from the polymerization of at least one ethylenic monomer, chosen, for example, from ethylene, and isobutylene, and of at least one block of an acrylic polymer such as, for example, from methyl methacrylate, mention may be made of copolymers chosen, for example, from poly(methyl methacrylate)/polyisobutylene diblock copolymers, poly(methyl methacrylate)/polyisobutylene triblock copolymers, and grafted copolymers containing a poly(methyl methacrylate) skeleton and polyisobutylene grafts.

As grafted block copolymers and block copolymers comprising at least one block resulting from the polymerization of at least one ethylenic monomer and of at least one block of a polyether chosen, for example, from ($C_2$-$C_{18}$)polyoxyalkylene, such as, polyoxyethylene and polyoxypropylene, mention may be made diblock and triblock copolymers chosen from polyoxyethylene/polybutadiene and polyoxyethylene/polyisobutylene.

It is also possible to use copolymers of ($C_1$-$C_4$)alkyl (meth)acrylates and ($C_8$-$C_{30}$) alkyl (meth)acrylates. Mention may be made, for example, of stearyl methacrylate/methyl methacrylate copolymer.

In this case, the at least one stabilizer may be chosen from grafted polymers and block polymers, so as to have better interfacial activity. The reason for this is that the blocks and grafts that are insoluble in the synthesis solvent provide greater coverage at the surface of the particles.

In one embodiment, when the liquid fatty phase comprises at least one silicone oil, the at least one stabilizer may be chosen, for example, from grafted block copolymers and block copolymers comprising at least one block of polyorganosiloxane type and at least one block of a free-radical polymer, a polyether, and a polyester, for example, polyoxy($C_2$-$C_{18}$)alkylene blocks and as a further example, polyoxypropylenated and polyoxyethylenated blocks.

When the liquid fatty phase comprises no silicone oil, the at least one stabilizer may be chosen from:
(a) grafted block copolymers and block copolymers comprising at least one block of polyorganosiloxane type and at least one block chosen from a free-radical polymer, a polyether, and a polyester,
(b) copolymers chosen from ($C_1$-$C_4$) alkyl acrylates, ($C_1$-$C_4$) methacrylates, ($C_8$-$C_{30}$) alkyl acrylates, and ($C_8$-$C_{30}$) alkyl methacrylates,
(c) grafted block copolymers and block copolymers comprising at least one block resulting from the polymerization of at least one ethylenic monomer containing conjugated ethylenic bonds, and at least one block chosen from at least one of a vinyl polymer, an acrylic polymer, a polyether, and a polyester.

Diblock polymers may be used, for example, as the at least one stabilizer.

According to yet another embodiment variant of the invention, the at least one first film-forming polymer may be present in dissolved form in a liquid fatty phase as defined above, which can also be referred to as a liposoluble polymer.

Examples of liposoluble polymers which may be mentioned are at least one copolymer of formula (I):

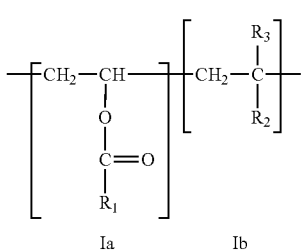

wherein:
- $R_1$ is chosen from linear and branched saturated hydrocarbon-based chains containing from 1 to 19 carbon atoms;
- $R_2$ is a group chosen from:
  a) —O—CO—$R_4$, wherein $R_4$ is chosen from linear and branched saturated hydrocarbon-based chains containing from 1 to 19 carbon atoms, with the proviso that $R_4$ is different from $R_1$ in the same at least one copolymer,
  b) —$CH_2$—$R_5$, wherein $R_5$ is chosen from linear and branched, saturated hydrocarbon-based chains containing from 5 to 25 carbon atoms,
  c) —O—$R_6$, wherein $R_6$ is chosen from saturated hydrocarbon-based chains containing from 2 to 18 carbon atoms, and
  d) —$CH_2$—O—CO—$R_7$, wherein $R_7$ is chosen from linear and branched, saturated hydrocarbon-based chains containing from 1 to 19 carbon atoms, and
- $R_3$ is chosen from:
  (1) a hydrogen atom when $R_2$ is chosen from the groups a), b) and c), and
  (2) a methyl group when $R_2$ is a group d), wherein the at least one copolymer comprises at least 15% by weight of at least one unit chosen from (Ia) and (Ib) wherein the saturated and branched hydrocarbon-based chains contain at least 7 carbon atoms.

The at least one copolymer of formula (I) is formed by the copolymerization of at least one vinyl ester (corresponding to the unit (Ia)) and of at least one other monomer (corresponding to the unit (Ib)) which may be chosen from α-olefins, alkyl vinyl ethers, allylic esters and methallylic esters.

When, in the unit (Ib), $R_2$ is chosen from the groups —$CH_2$—$R_5$, —O—$R_6$, and —$CH_2$—O—CO—$R_7$ as defined above, the at least one copolymer of formula (I) may comprise from 50 mol % to 95 mol % of at least one unit (Ia) and from 5 mol % to 50 mol % of at least one unit (Ib).

The at least one copolymer of formula (I) may also result from the copolymerization of at least one vinyl ester and of at least one other vinyl ester which is different from the first vinyl ester. In this case, these copolymers may comprise, for example, from 10 mol % to 90 mol % of at least one unit (Ia) and from 10 mol % to 90 mol % of at least one unit (Ib), wherein $R_2$ is a group —O—CO—$R_4$.

Among the vinyl esters leading to the unit chosen from formula (Ia), and formula (Ib) wherein $R_2$ is a group —O—CO—$R_4$, mention may be made of those chosen, for example, from vinyl acetate, vinyl propionate, vinyl butanoate, vinyl octanoate, vinyl decanoate, vinyl laurate, vinyl stearate, vinyl isostearate, vinyl 2,2-dimethyloctanoate and vinyl dimethylpropionate.

Among the α-olefins leading to the unit of formula (Ib), wherein $R_2$ is a group —$CH_2$—$R_5$, mention may be made of those chosen, for example, from 1-octene, 1-dodecene, 1-octadecene and 1-eicosene, and mixtures of α-olefins containing from 22 to 28 carbon atoms.

Among the alkyl vinyl ethers leading to the unit of formula (Ib), wherein $R_2$ is a group —O—$R_6$, mention may be made of those chosen, for example, from ethyl vinyl ether, n-butyl vinyl ether, isobutyl vinyl ether, decyl vinyl ether, dodecyl vinyl ether, cetyl vinyl ether, and octadecyl vinyl ether.

Among the allylic and methallylic esters leading to the unit of formula (Ib), wherein $R_2$ is a group —$CH_2$—O—CO—$R_7$, mention may be made of those chosen, for example, from allyl acetates, methallyl acetates, propionates, dimethylpropionates, butyrates, hexanoates, octanoates, decanoates, laurates, 2,2-dimethylpentanoates, stearates, and eicosanoates.

The at least one copolymer of formula (I) may also be crosslinked using at least one crosslinking agent which is intended to substantially increase their molecular weight.

This crosslinking is carried out during the copolymerization and the at least one crosslinking agent may be chosen, for example, from the vinyl type and the allylic or methallylic type. Non-limiting examples of the at least one crosslinking agent which may be mentioned are chosen, for example, from tetraallyloxyethane, divinylbenzene, divinyl octanedioate, divinyl dodecanedioate, and divinyl octadecanedioate.

Among the various at least one copolymer of formula (I) which may be used in the composition according to the invention, mention may be made of the following copolymers chosen, for example, from: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Liposoluble film-forming polymers which may also be mentioned are chosen, for example, from liposoluble homopolymers, such as those resulting from the homopolymerization of a vinyl ester containing from 9 to 22 carbon atoms, alkyl acrylates and alkyl methacrylates, wherein the alkyl groups contain from 10 to 20 carbon atoms.

Such liposoluble homopolymers may be chosen, for example, from polyvinyl stearate, polyvinyl stearate crosslinked with at least one compound chosen from divinylbenzene, diallyl ether and diallyl phthalate, polystearyl (meth)acrylate, polyvinyl laurate, and polylauryl (meth)acrylate, wherein the poly(meth)acrylates may optionally be crosslinked with the aid of at least one crosslinker chosen from ethylene glycol dimethacrylate and tetraethylene glycol dimethacrylate.

The liposoluble copolymers and homopolymers defined above are known and are disclosed, for example, in patent application FR-A-2 232 303; incorporated by reference, herein. They may have a weight-average molecular weight ranging from 2000 to 500,000, such as, for example, from 4000 to 200,000.

As liposoluble polymers which may be used in the invention, mention may also be made of polyalkylenes, for example, ($C_2$-$C_{20}$)alkylene copolymers, other than the polyolefin wax defined in a) of formula (I), chosen, for example, from polybutene, alkyllcelluloses with optionally saturated, linear and branched ($C_1$-$C_8$)alkyl groups (such as, for example, ethyl cellulose and propyl cellulose), vinylpyrrolidone (VP) copolymers, such as, for example, copolymers of vinylpyrrolidone and ($C_2$-$C_{40}$) alkenes such as, ($C_3$-$C_{20}$)alkenes. Non-limiting examples of VP copolymers which may be used in the invention, include VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene, and VP/acrylic acid/lauryl methacrylate copolymer.

The at least one first film-forming polymer may be present in the composition in a solids content ranging, for example, from 5% to 60% by weight relative to the total weight of the composition, such as, from 10% to 45% by weight and further still from 15% to 35% by weight relative to the total weight of the composition.

For example, the at least one first film-forming polymer and the at least one thermal transition agent may be present in the composition in a first film-forming polymer/thermal transition agent weight ratio ranging, for example, from 0.1:1 to 20:1, such as, from 0.5:1 to 10:1 and further such as from 1:1 to 8:1.

The composition may further comprise at least one dyestuff, chosen, for example, from pulverulent compounds and liposoluble dyes. The at least one dyestuff may be present in the composition in an amount ranging for example from 0.01% to 50% by weight relative to the total weight of the composition. The pulverulent compounds may be at least one compound chosen from pigments and nacres usually used in cosmetic compositions. The pulverulent compounds may be present in the composition according to the invention in an amount ranging, for example, from 0.1% to 25% by weight relative to the total weight of the composition, such as, from 1% to 20% by weight relative to the total weight of the composition.

The pigments may be white and colored and of mineral origin or organic origin. Among the mineral pigments which may be mentioned are titanium dioxide, optionally surface-treated, zirconium oxide, cerium oxide, iron oxide, chromium oxide, manganese violet, ultramarine blue, chromium hydrate and ferric blue. Non-limiting examples of organic pigments which may be mentioned are chosen from carbon black, pigments of D & C type and lakes based on cochineal carmine, barium, strontium, calcium, and aluminum.

The nacreous pigments may be chosen, for example, from white nacreous pigments, such as, mica coated with titanium and mica coated with bismuth oxychloride; colored nacreous pigments such as, for example, titanium mica with iron oxides, titanium mica with ferric blue, titanium mica with chromium oxide, titanium mica with an organic pigment of the above-mentioned type; and nacreous pigments based on bismuth oxychloride.

The composition may also comprise at least one filler which may be chosen from those that are well known to those skilled in the art and which are commonly used in cosmetic compositions. The at least one filler may be lamellar and spherical fillers of mineral origin and organic origin. Non-limiting examples of the at least one filler may be chosen, for example, from talc, mica, silica, kaolin, Nylon powder (ORGASOL from Atochem), poly-β-alanine powder, polyethylene powder, TEFLON, lauroyllysine, starch, boron nitride, tetrafluoroethylene polymer powders, hollow microspheres such as, for example, EXPANCEL (Nobel Industrie), POLYTRAP (Dow Corning), silicone resin microbeads (for example TOSPEARLS from Toshiba), precipitated calcium carbonate, magnesium carbonate, magnesium hydrocarbonate, hydroxyapatite, hollow silica microspheres (Silica Beads from Maprecos), glass microcapsules, ceramic microcapsules, and metal soaps derived from organic carboxylic acids containing from 8 to 22 and for example, from 12 to 18 carbon atoms, such as, zinc stearate, magnesium stearate, lithium stearate, zinc laurate, and magnesium myristate.

The composition may further comprise at least one additive usually used in such compositions, chosen for example, from fragrances, preserving agents, thickeners, surfactants, plasticizers, sequestrants, vitamins, proteins, ceramides, acidifying agents, basifying agents, emollients, sunscreens, free-radical scavengers, waxes, oils, and moisturizers.

Needless to say, a person skilled in the art will take care to select at least one of any of these optional additional compounds and the amount of any of these optional additional compounds, such that the advantageous properties of the composition according to the invention are not substantially adversely affected by the addition envisaged.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The examples which follow are intended to illustrate the invention without, however, limiting its scope.

Protocol to measure the water resistance of a film:

A layer of composition 300 μm thick (before drying) with an area of 9 cm×9 cm was spread onto a glass plate with an area of 10 cm×10 cm, and left to dry for 24 hours at 30° C. and 50% relative humidity. After drying, the plate was placed in a crystallizing vessel (diameter 19 cm; volume 2 liters) filled with 1 liter of water. The crystallizing vessel was then placed on a magnetic hotplate-stirrer sold under the name RCT BASIC by the company IKA Labortechnik.

A smooth PTFE cylindrical magnetic bar (length 6 cm; diameter 1 cm) was then placed on the film. The stirring speed was set to position 5. The water temperature was controlled using a thermometer at a temperature of 20° C. or 40° C. At time $t_0$=0, stirring was started. The time t (expressed in minutes) after which the film began to detach or loosen from the plate or when a hole the size of the magnetic stirring bar was observed, i.e. when the hole had a diameter of 6 cm, was measured. The test was stopped if the film remained intact at the end of 2 hours. The water resistance of the film corresponded to the time, t, measured.

EXAMPLES 1 to 8

Eight polycaprolactones (noted PCL) having the characteristics below were tested:

| Example | PCL(*) | Melting point (° C.) | OH number | Molecular weight |
|---------|--------|----------------------|-----------|------------------|
| 1 | CAPA240 | 68 | 28 | 4000 |
| 2 | CAPA223 | 48 | 56 | 2000 |
| 3 | CAPA222 | 53 | 56 | 2000 |
| 4 | CAPA217 | 44 | 90 | 1250 |
| 5 | CAPA215 | 45 | 90 | 1250 |
| 6 | CAPA212 | 45 | 112 | 1000 |
| 7 | CAPA210 | 38 | 112 | 1000 |
| 8 | CAPA205 | 39 | 135 | 830 |

(*)commercial name, sold by the company Solvay

Each polycaprolactones was tested in the following composition:

| | |
|---|---|
| Polyurethane as an aqueous dispersion, sold under the name Avalure UR 425 by the company Goodrich, at an active material content of 49% by weight | 24.5 g A.M. |

| | | |
|---|---|---|
| Polycaprolactone | | 10 g |
| Hydroxyethylcellulose | | 2 g |
| Black iron oxide | | 5 g |
| Propylene glycol | | 5 g |
| Preserving agents | qs | |
| Water | qs | 100 g |

For each composition, the resistance to cold water (maintained at 20° C.) and to hot water (maintained at 40° C.) were measured in accordance with the protocol above.

The following results were obtained:

| Example | 1 | 2 | 3 | 4 | 5 | 6 | 7 | 8 |
|---------|----|------|------|----|----|----|------|----|
| 20° C. | 40 | >120 | >120 | 60 | 26 | 45 | >120 | 19 |
| 40° C. | 11 | 2.5 | 5 | 5 | 7 | 15 | 14.5 | 4 |

It was found that, for each composition, the film was much less resistant in the presence of water at 40° C. (hot water) than in the presence of water at room temperature (cold water). The film was thus easier to remove with hot water and was more resistant to cold water.

EXAMPLE 9

A mascara having the composition below was prepared:

| | |
|---|---|
| Polyurethane as an aqueous dispersion, sold under the name AVALURE UR 425 by the company Goodrich, at an active material content of 49% by weight | 14 g A.M. |
| Polycaprolactone (CAPA 223 from the company Solvay) | 10 g |
| Ethyl alcohol | 5 g |
| Hydroxyethylcellulose | 1.9 g |
| Propylene glycol | 5 g |

| | | |
|---|---|---|
| Pigments | | 5 g |
| Preserving agents | qs | |
| Water | qs | 100 g |

The mascara applied easily to the eyelashes and showed good resistance to cold water. It was easily removed with hot water (40° C.).

This composition formed a film which had a resistance to cold water (20° C.) of 55 minutes (resistance measured according to the protocol described above) and a resistance to hot water (40° C.) of 3.5 minutes.

Comparative Examples 10 to 12

Two mascaras according to the invention (Examples 10 and 11) and a mascara not forming part of the invention (Example 12), having the compositions below, were prepared:

| | |
|---|---|
| Dispersion of polymer in isododecane | 60 g |
| Polycaprolactone | x g |
| Polyethylene wax (melting point = 83.9° C.) (Performalene 500 from the company Petrolite) | y g |
| Black iron oxide | 10 g |
| Mixture of oils* | 10 g |

*The oil mixture contained 1.43 g of octyldodecanol, 3.33 g of parleam oil, 1.91 g of polyvinylpyrrolidone eicosene (GANEX V220 from the company IFP) and 3.33 g of phenyltrimethicone (DOW CORNING 556 fluid).

| Example | 9 (I) | 10 (I) | 11 (NI) |
|---------|-------|--------|---------|
| X | 20 (CAPA 212) | 20 (CAPA 240) | 0 |
| Y | 0 | 0 | 20 |

I: invention;
NI: not in accordance with the invention

The Dispersion of Polymer In Isododecane Used:

A dispersion of non-crosslinked copolymer of methyl acrylate and acrylic acid in a 95/5 ratio, in isododecane, was prepared according to the method of Example 7 of document EP-A-749 747, incorporated by reference, herein. A dispersion of surface-stabilized particles of poly(methyl acrylate/acrylic acid) in isododecane with a polystyrene/copoly(ethylene-propylene) diblock copolymer sold under the name KRATON G1701 (Shell), having a solids content of 24.2% by weight and an average particle size of 180 nm and a Tg of 20° C., was thus obtained. This copolymer was able to form a film at room temperature.

For each composition, the resistance to cold water (20° C.) and to hot water (40° C.) of the deposited film was determined according to the protocol described in Examples 1 to 8, by measuring the time (expressed in minutes and seconds) after which the film begins to disintegrate.

The following results were obtained:

| Example | 10 (I) | 11 (I) | 12 (NI) |
|---------|--------|--------|---------|
| RT | 10 min 30 s | 54 min | 15 min |
| 40° C. | 2 min 30 s | 6 min | 10 min |

RT = Room temperature

It was found that, for Examples 10 and 11 according to the invention, the polycaprolactone substantially reduced the resistance to hot water of the film, while the polyethylene wax used in Example 12 reduced the resistance of the film to hot water very little. The compositions of Examples 10 and 11 according to the invention were thus easier to remove than composition 12 not forming part of the invention.

What is claimed is:

1. A cosmetic composition for a keratinous material comprising:
    at least one film-forming polymer; and
    at least one thermal transition agent chosen from semicrystalline compounds, which undergoes a change of state at a transition temperature, Tt, chosen within a temperature range from 25° C. to 80° C., the at least one thermal transition agent being not water-soluble in water maintained at a temperature below the transition temperature, Tt,
    wherein the at least one film-forming polymer and the at least one thermal transition agent are present in an amount which is sufficient so that the composition is capable, at the temperature of the keratinous material, of forming a film having a resistance (Rc) to hot water maintained at 40° C., of less than or equal to 15 minutes, and a resistance (Rf) to cold water, maintained at 20° C. such that Rf−Rc≧8 minutes, and further
    wherein said at least one film-forming polymer and said at least one thermal transition agent are different.

2. A composition according to claim 1, further comprising a physiologically acceptable medium.

3. A composition according to claim 1, wherein the film has a resistance (Rc) to hot water maintained at 40° C. of less than or equal to 12 minutes.

4. A composition according to claim 1, wherein the film has a resistance (Rc) to hot water maintained at 40° C. of less than or equal to 10 minutes.

5. A composition according to claim 1, wherein the film has a resistance (Rf) to cold water maintained at 20° C. water ranging from 8 to 120 minutes.

6. A composition according to claim 5, wherein the film has a resistance (Rf) to cold water maintained at 20° C. water ranging from 23 to 120 minutes.

7. A composition according to claim 1, wherein Rf−Rc≧10 minutes.

8. A composition according to claim 1, wherein the at least one thermal transition agent has a transition temperature ranging from 25° C. to 60° C.

9. A composition according to claim 8, wherein in the at least one thermal transition agent has a transition temperature ranging from 30° C. to 60° C.

10. A composition according to claim 1, further comprising at least one compound chosen from dyestuffs and fillers.

11. A composition according to claim 1, wherein the melting point of the at least one thermal transition agent ranges from 25° C. to 60° C.

12. A composition according to claim 11, wherein the melting point of the at least one thermal transition agent ranges from 30° C. to 60° C.

13. A composition according to claim 1, wherein the at least one thermal transition agent is chosen from polymers with a hydroxyl number of at least 5.

14. A composition according to claim 13, wherein the hydroxyl number is at least 25.

15. A composition according to claim 13, wherein the polymers with a hydroxyl number of at least 5 have a weight-average molecular weight of less than or equal to 10,000.

16. A composition according to claim 15, wherein the polymers with a hydroxyl number of at least 5 have a weight-average molecular weight ranging from 500 to 5000.

17. A composition according to claim 1, wherein the at least one thermal transition agent is chosen from polycaprolactones.

18. A composition according to claim 1, wherein the at least one thermal transition agent is present in the composition in an amount ranging from 0.1% to 30% by weight relative to the total weight of the composition.

19. A composition according to claim 18, wherein the at least one thermal transition agent is present in the composition in an amount ranging from 0.5% to 25% by weight relative to the total weight of the composition.

20. A composition according to claim 19, wherein the at least one thermal transition agent is present in the composition in an amount ranging from 3% to 15% by weight relative to the total weight of the composition.

21. A composition according to claim 1, wherein the at least one film-forming polymer is chosen from free-radical polymers, polycondensates of natural origin, and polymers of natural origin.

22. A composition according to claim 1, wherein the at least one film-forming polymer is chosen from vinyl polymers, polyurethanes, polyesters, and cellulose polymers.

23. A composition according to claim 1, wherein the at least one film-forming polymer is present in the form of particles dispersed in an aqueous medium.

24. A composition according to claim 23, wherein the particles dispersed in an aqueous medium are chosen from acrylic polymers and polyurethanes.

25. A composition according to claim 24, wherein the particles dispersed in an aqueous medium are chosen from polyurethanes.

26. A composition according to claim 23, wherein the particles dispersed in an aqueous medium ranges in size from 10 nm to 500 nm.

27. A composition according to claim 26, wherein the particles dispersed in an aqueous medium ranges in size from 20 nm to 300 nm.

28. A composition according to claim 23, further comprising at least one film-forming auxiliary which promotes the formation of a film with the at least one film-forming particles dispersed in an aqueous medium.

29. A composition according to claim 1, wherein the at least one film-forming polymer is present in the form of surface-stabilized particles dispersed in a liquid fatty phase.

30. A composition according to claim 29, wherein the surface-stabilized particles dispersed in a liquid fatty phase have a size ranging from 10 nm to 500 nm.

31. A composition according to claim 30, wherein the surface-stabilized particles dispersed in a liquid fatty phase have a size ranging from 20 nm to 300 nm.

32. A composition according to claim 29, wherein the liquid fatty phase comprises a volatile liquid fatty phase, optionally mixed with a non-volatile liquid fatty phase.

33. A composition according to claim 29, wherein the liquid fatty phase is present in the composition in an amount ranging from 5% to 98% by weight relative to the total weight of the composition.

34. A composition according to claim 33, wherein the liquid fatty phase is present in the composition in an amount ranging from 20% to 85% by weight relative to the total weight of the composition.

35. A composition according to claim 32, wherein the non-volatile liquid fatty phase is present in the composition in an amount ranging from 0% to 80% by weight relative to the total weight of the composition.

36. A composition according to claim 35, wherein the non-volatile liquid fatty phase is present in the composition in an amount ranging from 0.1% to 80% by weight relative to the total weight of the composition.

37. A composition according to claim 36, wherein the non-volatile liquid fatty phase is present in the composition in an amount ranging from 1% to 50% by weight relative to the total weight of the composition.

38. A composition according to claim 29, wherein the surface-stabilized particles are stabilized with at least one stabilizer chosen from block polymers, grafted polymers, and random polymers.

39. A composition according to claim 38, wherein the at least one stabilizer is chosen from grafted block polymers and block polymers comprising at least one block resulting from the polymerization of ethylenic monomers comprising at least one optionally conjugated ethylenic bond and at least one block of a styrene polymer.

40. A composition according to claim 29, wherein the liquid fatty phase comprises at least one oil chosen from oils of mineral origin, animal origin, plant origin, and synthetic origin, hydrocarbon-based oils, fluoro oils, and silicone oils.

41. A composition according to claim 29, wherein the liquid fatty phase is at least one compound chosen from:
  non-aqueous liquid compounds having a global solubility parameter according to the Hansen solubility space of less than 17 $(MPa)^{1/2}$, and
  monoalcohols having a global solubility parameter according to the Hansen solubility space of less than or equal to 20 $(MPa)^{1/2}$.

42. A composition according to claim 40, wherein said at least one oil is chosen from oils volatile at room temperature.

43. A composition according to claim 1, wherein the at least one film-forming polymer is present in the composition in a solids content ranging from 5% to 60% by weight relative to the total weight of the composition.

44. A composition according to claim 43, wherein the at least one film-forming polymer is present in the composition in a solids content ranging from 10% to 45% by weight relative to the total weight of the composition.

45. A composition according to claim 44, wherein the at least one film-forming polymer is present in the composition in a solids content ranging from 15% to 35% by weight relative to the total weight of the composition.

46. A composition according to claim 1, wherein the at least one film-forming polymer and the at least one thermal transition agent are present in the composition in a film-forming polymer/thermal transition agent weight ratio ranging from 0.1:1 to 20:1.

47. A composition according to claim 46, wherein the at least one film-forming polymer and the at least one thermal transition agent are present in the composition in a film-forming polymer/thermal transition agent weight ratio ranging from 0.5:1 to 10:1.

48. A composition according to claim 47, wherein the at least one film-forming polymer and the at least one thermal transition agent are present in the composition in a film-forming polymer/thermal transition agent weight ratio ranging from 1:1 to 8:1.

49. A composition according to claim 1, further comprising at least one additive chosen from thickeners, preserving agents, fragrances, sunscreens, free-radical scavengers, waxes, oils, moisturizers, vitamins, fillers, surfactants, plasticizers, sequestrants, proteins, ceramides, acidifying agents, basifying agents, and emollients.

50. A composition according to claim 1, wherein the composition is in a form chosen from a mascara, an eyeliner, a product for the lips, a blusher, an eyeshadow, a foundation, a make-up product for the body, a concealer product, a product for the nails, an anti-sun composition, a skin coloring composition, and a skincare product.

51. A mascara comprising, in a physiologically acceptable medium,
  at least one film-forming polymer, and
  at least one thermal transition agent chosen from semi-crystalline compounds, which undergoes a change of state at a transition temperature, Tt, chosen within a temperature range from 25° C. to 80° C., the at least one thermal transition agent being not water-soluble in water maintained at a temperature below the transition temperature, Tt,
  wherein the at least one film-forming polymer and the at least one thermal transition agent are present in an amount which is sufficient so that the composition is capable of forming a film, at the temperature of a keratinous material to which said mascara is applied,
  wherein the film has a resistance (Rc) to hot water maintained at 40° C. of less than or equal to 15 minutes, and a resistance (Rf) to cold water maintained at 20° C., such that Rf−Rc≧8 minutes, and
  wherein said at least one film-forming polymer and said at least one thermal transition agent are different.

52. A cosmetic care or make-up process for a keratinous material, comprising applying to the keratinous material a cosmetic composition comprising,
  at least one film-forming polymer, and
  at least one thermal transition agent chosen from semi-crystalline compounds which undergoes a change of state at a transition temperature, Tt, chosen within a temperature range from 25° C. to 80° C., the at least one thermal transition agent being not water-soluble in water maintained at a temperature below the transition temperature, Tt,
  wherein the at least one film-forming polymer and the at least one thermal transition agent are present in an amount which is sufficient so that the composition is capable, at the temperature of the keratinous material, of forming a film having a resistance (Rc) to hot water, maintained at 40° C., of less than or equal to 15 minutes, and a resistance (Rf) to cold water, maintained at 20° C., such that Rf−Rc≧8 minutes, and further
  wherein said at least one film-forming polymer and said at least one thermal transition agent are different.

53. A method for obtaining a film comprising, applying to a keratinous material a composition comprising,
  at least one film-forming polymer, and
  at least one thermal transition agent chosen from semi-crystalline compounds which undergoes a change of state at a transition temperature, Tt, chosen within a temperature range from 25° C. to 80° C., the at least one thermal transition agent being not water-soluble in water maintained at a temperature below the transition temperature, Tt,
  wherein the at least one film-forming polymer and the at least one thermal transition agent are present in an amount which is sufficient so that the composition is capable, at the temperature of the keratinous material, of forming a film having a resistance (Rc) to hot water, maintained at 40° C., of less than or equal to 15 minutes, and a resistance (Rf) to cold water, maintained at 20° C., such that Rf−Rc≧8 minutes, and further wherein said at least one film-forming polymer and said at least one thermal transition agent are different.

54. A process for removing make-up from a made-up keratinous material comprising, rinsing the made-up keratinous material with hot water maintained at a temperature of at least 35° C., wherein the made-up keratinous material is made-up with a composition comprising, at least one film-forming polymer, and at least one thermal transition agent chosen from semi-crystalline compounds which undergoes a change of state at a transition temperature, Tt, chosen within a temperature range from 25° C. to 80° C., the at least one thermal transition agent being not water-soluble in water maintained at a temperature below the transition temperature, Tt, wherein the at least one film-forming polymer and the at least one thermal transition agent are present in an amount which is sufficient so that the composition is capable, at the temperature of the keratinous material, of forming a film having a resistance (Rc) to hot water, maintained at 40° C., of less than or equal to 15 minutes, and a resistance (Rf) to cold water, maintained at 20° C., such that Rf−Rc≧8 minutes, and further wherein said at least one film-forming polymer and said at least one thermal transition agent are different.

55. A process according to claim 54, wherein the hot water contains no detergent.

56. A composition according to claim 1, further comprising an emulsifier, wherein the emulsifier is present in the composition in an amount less than 0.5% by weight relative to the total weight of the composition.

* * * * *